United States Patent [19]

Carbonnelle et al.

[11] 4,100,806
[45] Jul. 18, 1978

[54] SAMPLING ROD FOR CORROSIVE GASES OR FUMES IN AN INCINERATOR, PARTICULARLY WHEN INSTALLED ON A SHIP

[75] Inventors: Jacques Carbonnelle, Boulogne Billancourt; Gérard Chevalier, Orsay; Pierre Zettwoog, Le Perray en Yvelines, all of France

[73] Assignee: Commissariat a l'Energie Atomique, Paris Cedex, France

[21] Appl. No.: 767,620

[22] Filed: Feb. 10, 1977

[30] Foreign Application Priority Data

Apr. 2, 1976 [FR] France .............................. 76 09624

[51] Int. Cl.² ........................................... G01N 1/24
[52] U.S. Cl. ............................................ 73/421.5 A
[58] Field of Search ................. 73/421.5 A; 138/145, 138/146, 177, 178

[56] References Cited

U.S. PATENT DOCUMENTS

| | | | |
|---|---|---|---|
| 2,356,845 | 8/1944 | Hines | 73/421.5 A |
| 2,814,952 | 12/1957 | Ryant et al. | 73/421.5 R |
| 2,926,527 | 3/1960 | Crandall | 73/421.5 A |
| 3,085,438 | 4/1963 | St John | 138/145 |
| 3,226,101 | 12/1965 | Balaz et al. | 138/146 |

*Primary Examiner*—S. Clement Swisher
*Attorney, Agent, or Firm*—McNenny, Pearne, Gordon, Gail, Dickinson & Schiller

[57] ABSTRACT

Sampling rod for corrosive gases or fumes in an incinerator, particularly when installed on a ship.

It comprises in a coaxial construction a central tube for the suction of gases made from a plastic material resistant to the corrosion by these high temperature gases, a first metallic tube forming a reinforcement for the central tube and enveloping the latter, a second metallic tube surrounding the first tube and defining with the latter an annular space traversed by a liquid fluid for the cooling of the gases circulating in the central tube and for maintaining said gases at an appropriate temperature, a layer of a thermally insulating material having a fibrous structure surrounding the second metallic tube and an outer jacket made from a refractory material which resists the mechanical and thermal shocks and ensures the distribution of the external heat in the insulating material.

7 Claims, 2 Drawing Figures

SAMPLING ROD FOR CORROSIVE GASES OR FUMES IN AN INCINERATOR, PARTICULARLY WHEN INSTALLED ON A SHIP

BACKGROUND OF THE INVENTION

The present invention relates to a rod for sampling the gases or fumes produced by an incinerator for industrial refuse or waste having a high toxicity level for the purpose of continuously analysing the content of said gases in order to relate this content to the value of the dosage permitted for discharge into the atmosphere and, if necessary, to permit the stoppage of combustion in the furnace in the case where the said limiting dosage is exceeded.

The invention is applied more particularly to the case of incinerating waste of organo-chlorinated products having therefore a high content of water-soluble hydrochloric acid and aims more particularly at the design of a sampling rod associated with a furnace or identical installation which is mounted on an incinerator ship discharging the gaseous effluents resulting from the combustion of the said waste material into the atmosphere off the coast.

It can be readily understood that within the framework of the more specifically envisaged application the discharge of gases and fumes resulting from the combustion of organo-chlorinated waste must be carefully controlled, more particularly with a view to avoiding pollution of surrounding waters by doses of toxic products higher than those normally tolerated. However, serious difficulties are encountered in continuously sampling combustion gases or fumes and in passing said samples to an analyser without modifying the composition of said gases and more particularly their content of hydrochloric acid and organo-chlorinated derivative vapours, due particularly to the solubility of these substances in the water present in the form of moisture in the surrounding atmosphere. In particular, such a sampling process should be carried out directly on leaving the combustion area in the furnace, that is to say in an area where the temperature of the gases is generally very high, namely of the order of 1000° to 1200° C. When sampling takes place at a greater distance from said area, it is not satisfactory because the gas collected is then at least partly diluted by the ambient air and the water. Moreover, account must be taken of meteorological conditions at the time of sampling, said conditions varying significantly and rapidly at sea, particularly as a function of the direction of the prevailing winds and which preponderantly influence the content of the collected gases when sampling takes place at a significant distance from the combustion area.

It is finally necessary for the sampling apparatus used to be appropriately protected both internally and externally against corrosion by gases and by sea air. Due to the variations in the force and direction of the wind, those parts of the rod located closest to the furnace wall are sometimes in the flow of the combustion gases and at other times in a flow of cold moist air, thus locally creating significant thermal shocks.

The necessity of sampling without any dilution or modification in the composition of the gases in an area where the corrosive gases are at very high temperature and where the rod is subject to the thermal radiation from the furnace walls causes problems with regard to the nature of the materials used for the rod and the structure of its different parts, whereby the highly toxic nature of the gases collected makes the solution of these problems even more difficult. The operation of such a rod in a marine installation with the inevitable vibrations and constant rocking of the carrying vessel makes the adaptation of conventional methods completely unsuitable.

BRIEF SUMMARY OF THE INVENTION

The invention has for its object a rod for the direct sampling of gases or fumes in an incineration furnace, more particularly a furnace carried by an incinerator ship, which makes it possible to obviate these disadvantages due to the composite construction of the rod where the outflow of gases sampled by a suction process takes place in a plastic tube which is relatively insensitive to corrosion, said tube being permanently cooled to limit the action of heat, whereby an outer refractory jacket provides a suitable resistance to thermal shocks and the corrosive action of gases in the furnace, as well as to the marine environment.

To this end the sampling rod comprises in a coaxial construction a central tube for the suction of gases made from a plastic material resistant to the corrosion by these high temperature gases, a first metallic tube forming a reinforcement for the central tube and enveloping the latter, a second metallic tube surrounding the first tube and defining with the latter an annular space traversed by a liquid fluid for the cooling of the gases circulating in the central tube and for maintaining said gases at an appropriate temperature, a layer of a thermally insulating material having a fibrous structure surrounding the second metallic tube and an outer jacket made from a refractory material which resists the mechanical and thermal shocks and ensures the distribution of the external heat in the insulating material.

According to a preferred embodiment of the invention, the space between the first and second metallic tubes traversed by the cooling fluid is separated into two annular and coaxial regions by an intermediate tube open at its end adjacent to that where the gases enter the central tube, whereby the cooling fluid is circulated in such a way that the outflow of said fluid firstly takes place in the annular region defined between the intermediate tube and the second metallic tube and then in the annular region between the intermediate tube and the first metallic tube, said two regions being connected respectively to a fluid supply tube and a fluid discharge tube by orifices provided in the ends of the second tube and of the intermediate tube opposite to the end of the central tube via which the entry of the sampled gases takes place.

Preferably the central tube is extended beyond the two metallic tubes downstream of the cooling fluid supply and discharge tubes and issues into the casing of a compressed air pump, creating in the central tube a suction vacuum of the gases to be sampled, whereby at least a fraction of said gases is tapped upstream of the pump into a pipe connected to the central tube on the one hand and to an apparatus for analysing the content of said gases on the other hand.

The invention also relates to an installation utilising a sampling rod whose characteristics are described hereinbefore and comprising more particularly a rocking support on which is articulated the rod at its end opposite to that via which the gases pass into the central tube, said support having a jack articulated on the rod to ensure the raising or substantially horizontal positioning of the latter with the end of the central tube in the sampling area. Advantageously the rocking support has a protective shield mounted between the sampling area and the support.

BRIEF DESCRIPTION OF THE DRAWINGS

Other features of the rod for sampling gases or fumes in an incinerator according to the present invention can be gathered from the following description with regard to an embodiment given in an illustrative and non-limitative manner with reference to the attached drawings, wherein show.

DETAILED DESCRIPTION OF THE PREFERRED EMBODIMENTS

Figure 1:
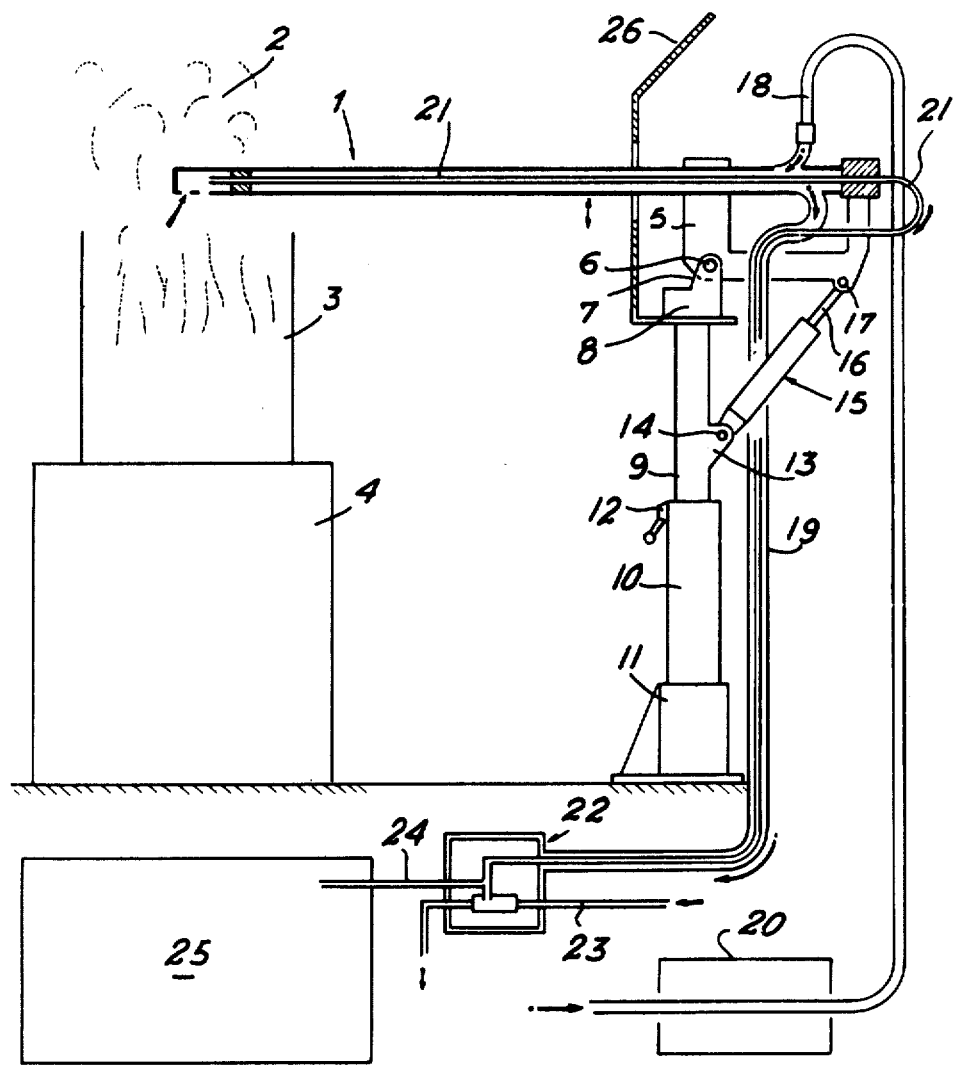
FIG. 1, a schematic view of an installation for sampling gases or fumes using a rod according to the invention.

The installation illustrated in generally schematic manner in FIG. 1 shows the sampling rod 1 in a position where the latter is carrying out the sampling of very toxic gases or fumes in a plume 2 leaving the upper section 3 of a furnace 4, relative to which the detailed construction has little bearing on the present invention. In the present specific application this furnace serves to incinerate industrial waste or refuse and particularly organo-chlorinated waste with the discharge of the gaseous effluents produced at sea off the coast. Thus, said furnace is installed on an incinerator ship (not shown) which, quite apart from the vibrations and rocking of the ship, makes said sampling difficult because the furnace cannot have a very high discharge pipe or stack as is the case with installations on land. Thus, sampling carried out without special precautions could not be representative of the exact content of the particles of combustion gases because the isokinetism of the speeds cannot be appropriately effected. Rod 1 must be designed in such a way that it can be brought as close as possible to the axis of the furnace and to a very small distance from its upper section at a point where the gases are at very high temperature, namely of the order of 1000 ° to 1200 ° C, whereby in addition the rod is subject to very considerable thermal radiation by the walls of the furnace.

To this end rod 1 is supported at its end opposite to that via which the sampled gases enter by a right-angled member 5 articulated about a transverse spindle 6 on a cover 7 provided on head 8 of a sliding rod 9 permitting the adjustment of the height of the rod. To this end the sliding rod can move in a fixed shaft 10 supported in the vertical position by a mounting 11, whereby the immobilisation of sliding rod 9 in shaft 10 at an appropriate height is assured by a lateral locking member 12. On rod 9 is provided a plate 13 whereon is articulated about a spindle 14 the body 15 of a hydraulic jack whose rod 16 is itself articulated about a spindle 17 on the end of the right-angled member 5. Thus, said jack permits the pivoting of member 5 and of rod 1 supported by the latter in such a way that the end of rod 1 is brought into or removed from the plume 2 of gases or fumes leaving furnace 4.

Although a detailed description of the sampling rod 1 is provided hereinafter relative to FIG. 2, it can be seen in FIG. 1 that said rod is connected to two tubes 18 and 19 permitting the circulation of an appropriate liquid cooling fluid within the rod, whereby the initial temperature of said fluid and more specifically at the start of heating of the furnace is adjusted by a heater 20 comprising, for example, an electric resistance. The gases sampled in plume 2 are sucked into rod 1 by a central tube 21, whereby the latter is extended beyond the horizontal end of the rod and is connected to a suction box 22. At the latter terminates a compressed air supply tube 23 and a tapping pipe 24 connected to tube 21 in such a way that at least a fraction of the sampled gases circulating in the tube are passed to an analytical apparatus 25 whose characteristics are claimed in French Application No. EN 7,609,625 filed by the COMMISSARIAT A L'ENERGIE ATOMIQUE for "Process and apparatus for the analysis of a mixture of hydrochloric acid and organo-chlorinated compounds contained in gases resulting more particularly from the incineration of organo-chlorinated compounds". Finally, rod 9 of the support of rod 1 has a protective shield 26 located between said support and the wall of incinerator 4.

Figure 2:
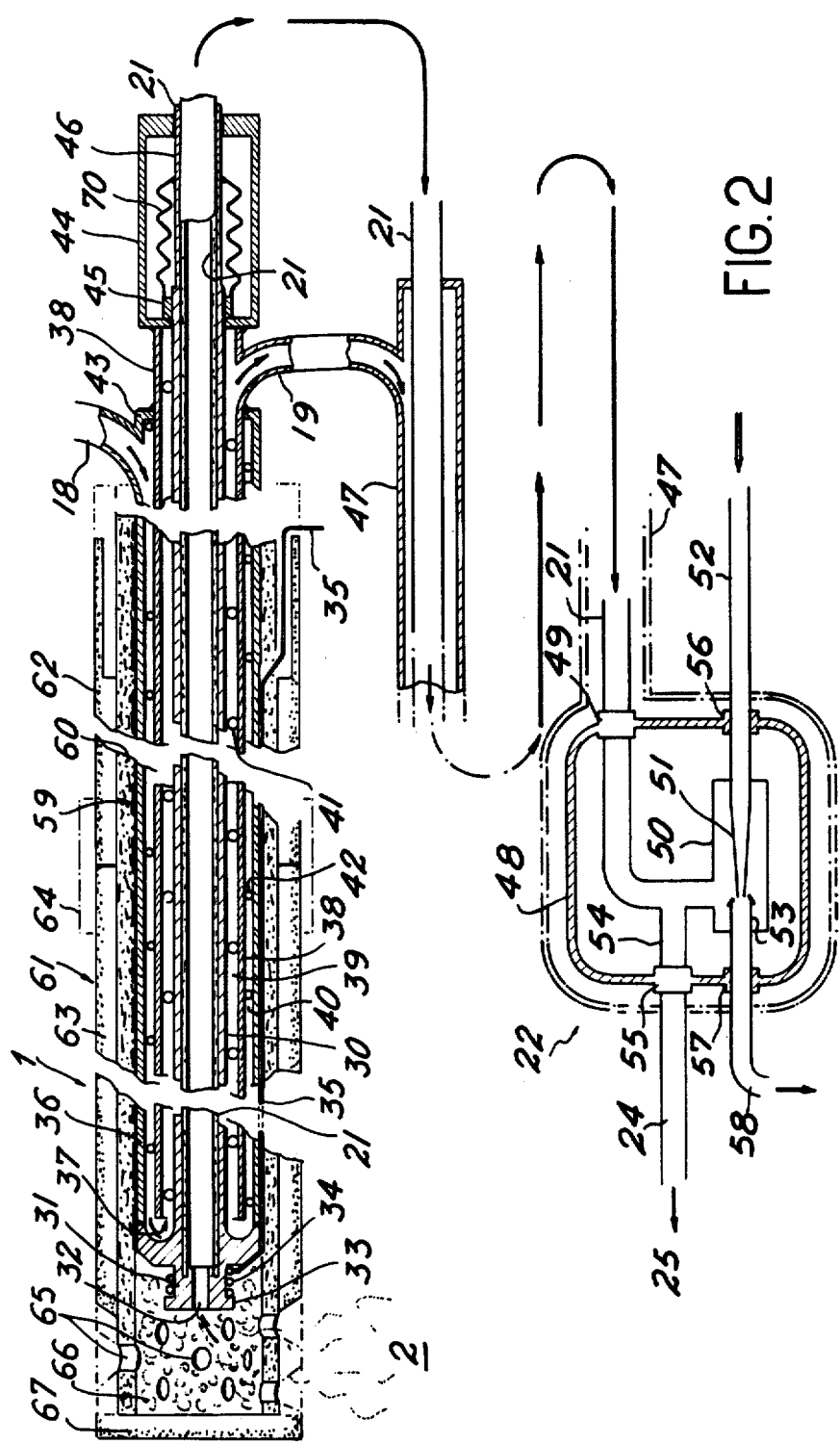
FIG. 2, a larger scale detailed view in partial longitudinal section of the sampling rod with the means associated therewith for ensuring on the one hand the cooling of the sampled gases, and on the other the suction of said gases.

FIG. 2 illustrates in greater detail the special construction of the sampling rod according to the invention. This drawing shows more particularly the central tube 21 via which the gases from plume 2 emanating from the furnace are sucked into the rod, whereby said central tube is made from a suitable plastic material and preferably polytetrafluoroethylene "Teflon" which has an excellent chemical inertia relative to organic vapours, together with a good resistance to hydrochloric acid and a remarkable stability at temperatures of the order of 250° and above. The outer surface of central tube 2 is surrounded by a first metallic tube 30, more specifically made from mild steel serving as a reinforcement for tube 21 by externally holding it in place. The end of metallic tube 30 adjacent to that via which the gases are sucked into central tube 21 has an end fitting 31 having an axial bore 32 arranged in the axis of tube 21 for the passage of said gases. This end fitting 31 also has a terminal flange 33 permitting the fitting onto the outer surface of the end fitting of at least one temperature measuring probe 34 connected at the outside of the rod by an electrical connection 35 to an appropriate not shown reading member.

The first metallic tube 30 arranged around the central tube 21 is in turn surrounded by a second metallic tube 36 which is appropriately spaced relative to the first tube in such a way that between the said tubes is defined an annular space 37 reserved for the circulation of a fluid for cooling the gases during the suction thereof into tube 21 during their passage in the latter. Preferably said annular space 37, which is sealed at its end adjacent to that via which the gases enter by end fitting 31 is sub-divided by an intermediate metallic tube 38 also made from mild steel into two coaxial annular regions 39 and 40. Region 39 defined between intermediate tube 38 and the first metallic tube 30 is connected to the discharge tube 19 whilst space 40 defined between the said intermediate tube 38 and the second metallic tube 36 is connected to supply tube 18. Advantageously each of the two annular regions 39 and 40 has a reinforcing member 41 and 42 comprising a metallic wire or the like wound helically onto the first tube 30 and onto intermediate tube 38, said reinforcements permitting the definition in the corresponding spaces an enveloping path for the outflow of the cooling fluid in its double passage about the central tube 21.

Although the nature of the cooling fluid does not per se form a special feature of the invention, preference is given to a liquid known under the name "Gilotherme" (Registered Trade Mark) which is an organic liquid formed from a mixture of diphenyl and terphenyl and has a good behaviour at the temperature of use due to its high boiling point and its significant heat conduction coefficient. In an effectively performed example of use, the speed of said fluid in the rod was chosen as about 1.5 m/sec. representing a flow rate of 0.15 l/sec. for a temperature variation of 40° C between the inlet and outlet of the rod with a minimum operating temperature in the central tube of 130° C and an average temperature of 150° C.

Thus, supply tube 18 communicates with the annular region 40, itself closed at the end of the rod by a return line 43 provided at the end of the second tube 36. In the same way, annular region 39 connected to the discharge tube 19 is defined by the intermediate tube 38 which is extended to an expansion box 44 where the end 45 of the first metallic tube 30 emerges. This end is connected to a second tube 46 of the same diameter provided at the other end of the box via an expansion bellows 70. The Teflon central tube 21 freely traverses bellows 70 and is extended beyond box 44 and in the embodiment in question traverses a manifold 47 which collects the cooling fluid when it leaves tube 19. Tube 21 and manifold 47 are then continued up to the suction box 22 having a tight casing 48 maintained at an appropriate temperature by the circulation of the cooling fluid. Tube 21 traverses the wall of the latter via a union 49 whilst manifold 47 surrounds the box.

Within casing 48 the end of tube 21 issues into a sleeve 50 of an air pump constituted by an injector 51 mounted at the end of a compressed air admission tube 52 and a venturi 53. In casing 48 tube 21 is also connected to tapping pipe 54 in such a way that at least a fraction of the gases sucked through tube 21 due to the vacuum created by the compressed air pump is branched into pipe 24, and after traversing a sealed passage 55, is directed to analyser 25, (FIG. 1). Two other sealed passages 56 and 57 are provided in the casing 48 for tube 52 and a discharge tube 58 for the compressed air and the remainder of the entrained gases.

Returning again to the actual sampling rod, it can be seen that the outer surface of the second metallic tube 36 is covered by a protective coating 59 constituted by a non-corroding plastic material and more specifically based on polytetrafluoroethylene. In turn, tube 36 is surrounded by a thermally insulating layer 60 of appropriate thickness, preferably constituted by a material based on silico-aluminous fibres with a diameter of a few microns and without any organic binder between them, for example the commercial product marketed under the Registered Trade Mark "Kaowool" whose melting temperature of about 1700° C is well above the maximum temperature of use in continuous service of the rod of about 1250° C. Layer 60 is in turn surrounded by an outer jacket 61 made from several successive parts 62 and 63 interconnected by adapted connecting members 64. Advantageously jacket 61 is made from a highly refractory material, more particularly based on silicon carbide of the type marketed under the Registered Trade Mark "Crystar" whereby such a material can be used up to a temperature of about 1750° C. The end of the outer jacket 61 surrounding end fitting 31 has a series of holes 65 emitting the gases or fumes sampled from plume 2 to enter the rod after traversing a filter 66, specifically made from silica wool preventing the suction into the rod of any solid particles. Finally, jacket 61 is closed at its end by a disc 67 of the same type.

In this way a sampling rod is obtained of simple design and which is particularly well suited to the envisaged utilisation in an incinerator for organo-chlorinated waste containing between 15 and 70% chlorine. The gaseous effluents discharged by the incinerator and sampled by the cane at between 1100° and 1200° C, more particularly contain about 10% oxygen and between 10 and 60 g/m$^3$ hydrochloric acid reduced to normal pressure and temperature conditions. These especially corrosive gases can still be sampled continuously due to the central polytetrafluoroethylene tube and the permanent cooling of said tube. The thermal protection relative to the outside atmosphere is obtained by the outer jacket and the insulating covering surrounding the metallic circulating tubes. It should finally be noted that the basic concept of the sampling process prevents the dilution of the sampled gas and particularly of the hydrochloric acid contained therein, sampling being carried out at a temperature above the dew point of the constituents of the gas, thus preventing any deposition on the inside of the rod by physical or chemical adsorption on its walls.

The rod is used in the following manner:

On lighting the furnace the sampling rod is brought into the area above the outlet for the gaseous effluents in such a way that the temperature of the rod rises at the same time and at the same speed as the internal refractory lining or the bricks of the furnace so as to prevent too sudden thermal shocks in the actual sampling phase. In particular the rod is tilted on its support to extend substantially horizontally above the furnace as close as possible to the combustion area, whereby the circulation of cooling fluid in the rod is simultaneously controlled to ensure the thermal protection of the central plastic tube. Once thermal equilibrium has been established suction of the gases takes place by the air pump connected to the central tube whose nature prevents any danger of corrosion. The outer refractory jacket which is permanently subject to the gaseous effluents and to the outside atmosphere, more particularly sea air, in turn ensures the external protection of the rod. During a stoppage of the furnace the refrigerating system is maintained in operation for as long as the outer portions of the rod are subject to high temperatures, after which the rod is removed until a new operating cycle commences.

Using a central tube with an outside diameter of 12 mm, metallic tubes with diameters of 17.2 and 33.7 mm, a 9 mm thick insulating layer and a 76 mm silicon carbide tube, gas sampling operations were carried out at 1100° C at the rod inlet, said gases being cooled in the latter to an average temperature of 150° C with a flow rate of 5 l/min., the quantity of heat eliminated by the cooling fluid being approximately 2.4 kcal/sec.

Obviously the invention is not limited to the embodiment described and represented hereinbefore, and in fact covers all variants thereof.

What is claimed is:

1. A sampling rod for corrosive gases or fumes in an incinerator comprising in a coaxial construction a central tube for the suction of gases made from a plastic material resistant to the corrosion by these high temperature gases, a first metallic tube forming a reinforcement for the central tube and enveloping the latter, a second metallic tube surrounding the first tube and defining with the latter an annular space traversed by a liquid fluid for the cooling of the gases circulating in the central tube and for maintaining said gases at an appropriate temperature, a layer of a thermally insulating material having a fibrous structure surrounding the second metallic tube and an outer jacket made from a refractory material which resists the mechanical and thermal shocks and ensures the distribution of the external heat in the insulating material, the space between the first and second metallic tubes traversed by the cooling fluid being separated into two annular and coaxial regions by an intermediate tube open at its end adjacent to that where the gases enter the central tube, whereby the cooling fluid is circulated in such a way that the outflow of said fluid firstly takes place in the annular region defined between the intermediate tube and the second metallic tube and then in the annular region between the intermediate tube and the first metallic tube, said two regions being connected respectively to a fluid supply tube and a fluid discharge tube at locations opposite to the end of the central tube via which the entry of the sampled gases takes place, the central tube extending axially beyond the two metallic tubes downstream of the cooling fluid supply and discharge tubes to issue into the casing of a compressed air pump thus creating in the central tube a suction vacuum of the gases to be sampled, an apparatus for analyzing the content of said gases, another tube extending to said analyzing apparatus and being connected to said central tube at a location upstream of the pump, a rocking support on which is articulated the sampling rod at its end opposite to that via which the gases pass into the central tube, and an extendable jack articulated on the rod to ensure the raising or substantially horizontal positioning of the latter with the end of the central tube in the sampling area.

2. A sample rod according to claim 1, including a second extendable jack, and said rocking support and first mentioned extendable jack are disposed on said second extendable jack.

3. A sampling rod for corrosive gases or fumes in an incinerator comprising in a coaxial construction a central tube for the suction of gases made from a plastic material resistant to the corrosion by these high temperature gases, a first metallic tube forming a reinforcement for the central tube and enveloping the latter, a second metallic tube surrounding the first tube and defining with the latter an annular space traversed by a liquid fluid for the cooling of the gases circulating in the central tube and for maintaining said gases at an appropriate temperature, a layer of a thermally insulating material having a fibrous structure surrounding the second metallic tube and an outer jacket made from a refractory material which resists the mechanical and thermal shocks and ensures the distribution of the external heat in the insulating material, the space between the first and second metallic tubes traversed by the cooling fluid being separated into two annular and coaxial regions by an intermediate tube open at its end adjacent to that where the gases enter the central tube, whereby the cooling fluid is circulated in such a way that the outflow of said fluid firstly takes place in the annular region defined between the intermediate tube and the second metallic tube and then in the annular region between the intermediate tube and the first metallic tube, said two regions being connected respectively to a fluid supply tube and a fluid discharge tube at locations opposite to the end of the central tube via which the entry of the sampled gases takes place, the central tube extending axially beyond the two metallic tubes downstream of the cooling fluid supply and discharge tubes to issue into the casing of a compressed air pump thus creating in the central tube a suction vacuum of the gases to be sampled, an apparatus for analyzing the content of said gases, another tube extending to said analyzing apparatus and being connected to said central tube at a location upstream of the pump, a cooling jacket surrounding said central tube from a location spaced from said supply and discharge tubes to a location near said pump, and means hydraulically connecting said discharge tube and said jacket whereby said cooling fluid flows from said two regions to said cooling jacket.

4. A sample rod according to claim 3, including a fluid tight housing, said pump being disposed within said housing, and said jacket being hydraulically connected to said housing whereby said cooling fluid flows from said cooling jacket to said housing.

5. A sampling rod for corrosive gases or fumes in an incinerator comprising in a coaxial construction a central tube for the suction of gases made from a material resistant to the corrosion by the high temperature gases, a cooling tube surrounding the central tube and defining an annular space traversed by a liquid fluid for the cooling of the gases circulating in the central tube and for maintaining said gases at an appropriate temperature, a fluid supply tube and a fluid discharge tube hydraulically connected to said annular space at locations opposite to the end of the central tube via which the entry of the sampled gases takes place, said central tube extending axially beyond the cooling tube downstream of the cooling fluid supply and discharge tubes to a compressed air pump thus creating in the central tube a suction vacuum of the gases to be sampled, an apparatus for analyzing the content of said gases, another tube extending to said analyzing apparatus and being connected to said central tube at a location upstream of the pump, a cooling jacket surrounding said central tube from a location spaced from said supply and discharge tubes to a location near said pump, and means hydraulically connecting said discharge tube and said jacket whereby said cooling fluid flows from said annular space to said cooling jacket.

6. A sample rod according to claim 5, including a fluid tight housing, said pump being disposed within said housing, and said jacket being hydraulically connected to said housing whereby said cooling fluid flows from said cooling jacket to said housing.

7. A sampling rod for corrosive gases or fumes in an incinerator comprising in a coaxial construction a central tube for the suction of gases made from a material resistant to the corrosion by the high temperature gases, a cooling tube surrounding the central tube and defining an annular space traversed by a liquid fluid for the cooling of the gases circulating in the central tube and for maintaining said gases at an appropriate temperature, a fluid supply tube and a fluid discharge tube hydraulically connected to said annular space at locations opposite to the end of the central tube via which the entry of the sampled gases takes place, said central tube extending axially beyond the cooling tube downstream of the cooling fluid supply and discharge tubes to a compressed air pump thus creating in the central tube a suction vacuum of the gases to be sampled, an apparatus for analyzing the content of said gases, another tube extending to said analyzing apparatus and being connected to said central tube at a location upstream of the pump, a first pivot connection pivotally connecting said central tube and cooling tube and supply and discharge tubes to a member, an extendable jack having one end pivotally connected to said member and another end pivotally connected to said central tube and cooling tube and supply and discharge tubes, and said member being a part of a second extendable jack.

* * * * *